United States Patent [19]
Elliott et al.

[11] Patent Number: 5,985,886
[45] Date of Patent: Nov. 16, 1999

[54] ENDOTHELIN RECEPTOR ANTAGONISTS

[75] Inventors: John Duncan Elliott, Wayne; Deborah Lynne Bryan, West Chester, both of Pa.

[73] Assignee: SmithKline Beecham Corporation, Philadelphia, Pa.

[21] Appl. No.: 09/097,756

[22] Filed: Jun. 16, 1998

Related U.S. Application Data

[62] Division of application No. 08/716,347, filed as application No. PCT/US96/12582, Aug. 2, 1996.
[60] Provisional application No. 60/001,791, Aug. 2, 1995, and provisional application No. 60/011,148, Feb. 1, 1996.
[51] Int. Cl.$^6$ .................................................. A01N 43/40
[52] U.S. Cl. .................... 514/277; 514/340; 514/357; 546/337; 546/268.4; 544/243
[58] Field of Search ..................... 514/269, 274, 514/256, 318; 546/268.4, 337; 548/253

[56] References Cited

U.S. PATENT DOCUMENTS

| | | | |
|---|---|---|---|
| 3,946,026 | 3/1976 | Meyer et al. | 260/295.5 |
| 4,886,816 | 12/1989 | Franckowiak et al. | 514/338 |
| 4,952,592 | 8/1990 | Torija et al. | 514/338 |
| 5,420,133 | 5/1995 | Dhanoa et al. | 514/256 |

FOREIGN PATENT DOCUMENTS

| | | |
|---|---|---|
| 0 861 831 A1 | 9/1998 | European Pat. Off. . |
| WO 96/30358 | 10/1996 | WIPO . |

*Primary Examiner*—Johann Richter
*Assistant Examiner*—Ebenezer Sackey
*Attorney, Agent, or Firm*—Linda E. Hall; Stephen A. Venetianer; Charles M. Kinzig

[57] ABSTRACT

Novel indane and indene derivatives are described which are endothelin receptor antagonists.

14 Claims, No Drawings

ENDOTHELIN RECEPTOR ANTAGONISTS

This is a divisional of application Ser. No. 08/716,347 filed Sep. 22, 1996, which is a 371 of PCT/US96/12582, filed Aug. 2, 1996; which claims priority front application Ser. No. 60/001,791, filed Aug. 2, 1995 and application Ser. No. 60/011,148, filed Feb. 1, 1996.

The present invention relates to pyridines, pyrimidines, pyrazines, pyridazines and triazines, pharmaceutical compositions containing these compounds and their use as endothelin receptor antagonists.

Endothelin (ET) is a highly potent vasoconstrictor peptide synthesized and released by the vascular endothelium. Endothelin exists as three isoforms. ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemnia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arterial blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity, radio contrast induced renal failure and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols el al. *Br. J. Pharm.* 99: 597–601, 1989 and Clozel and Clozel, *Circ. Res.*, 65: 1193–1200, 1989) coronary vasospasm (Fukuda et al., *Eur. J. Pharm.* 165: 301–304, 1989 and Lúscher, Circ. 83: 701, 1991) heart failure, proliferation of vascular smooth muscle cells, (Takagi, *Biochem & Biophys. Res. Commun.*; 168: 537–543, 1990, Bobek el. al., *Am. J. Physiol.* 258:408–C415, 1990) and atherosclerosis, (Nakaki et al., *Biochem. & Biophys. Res. Commun.* 158: 880–881, 1989, and Lerman et al., *New Eng. J. of Med.* 325: 997–1001, 1991). Increased levels of endothelin have been shown after coronary balloon angioplasty (Kadel et al., No. 2491 *Circ.* 82: 627, 1990).

Further, endothelin has been found to be a potent constrictor of isolated mammalian airway tissue including human bronchus (Uchida et al. *Eur. J. of Pharm.* 154: 227–228 1988, LaGente, *Clin. Exp. Allergy* 20: 343–348, 1990; and Springall et al., *Lancet*, 337: 697–701, 1991). Endothelin may play a role in the pathogenesis of interstitial pulmonary fibrosis and associated pulmonary hypertension, Glard et al., Third International Conference on Endothelin, 1993, p. 34 and ARDS (Adult Respiratory Distress Syndrome), Sanai et al., Supra, p. 112.

Endothelin has been associated with the induction of hemorrhagic and necrotic damage in the gastric mucosa (Whittle et al., *Br. J. Pharm.* 95: 1011–1013, 1988); Raynaud's phenomenon, Cinniniello et al., *Lancet* 337: 114–115, 1991); Crohn's Disease and ulcerative colitis, Munch et al., *Lancet*, Vol. 339, p. 381: Migraine (Edmeads, Headache, February 1991 p 127); Sepsis (Weitzberg et al., *Circ. Shock* 33: 222–227, 1991; Pittet et al.,*Ann. Surg.* 213: 262–264, 1991), Cyclosporin-induced renal failure or hypertension (*Eur. J. Phamacol.*, 180: 191–192, 1990, *Kidney Int*, 37: 1487–1491, 1990) and endotoxin shock and other endotoxin induced diseases (*Biochem. Biophys. Res. Commun.*, 161: 1220–1227, 1989, *Acta Physiol. Scand*, 137: 317–318, 1989) and inflammatory skin diseases. (*Clin Res.* 41:451 and 484, 1993).

Endothelin has also been implicated in preciampsia of pregnancy. Clark et al.,*Am. J. Obstet. Gynecol.* March 1992, p. 962–968; Kamor et al., *N. Eng. J. of Med.*, Nov. 22, 1990. p. 1486–1487; Dekker et al., *Eur. J. Ob. and Gyn. and Rep. Bio.* 40 (1991) 215–220: Schiff et al.,*Am. J. Ostet. Gynecol.* February 1992. p. 624–628; diabetes mellitus, Takahashi et al., *Diabetologia* (1990) 33:306–310; and acute vascular rejection following kidney transplant. Watschinger et al., *Transplantation* Vol. 52. No. 4, pp. 743–746.

Endothelin stimulates both bone resorption and anabolism and may have a role in the coupling of bone remodeling. Tatrai et al. *Endocrinology*, Vol. 131, p. 603–607.

Endothelin has been reported to stimulate the transport of sperm in the uterine cavity, Casey et al., *J. Clin. Endo and Metabolism*, Vol. 74, No. 1. p. 223–225, therefore endothelin antagonists may be useful as male contraceptives. Endothelin modulates the ovarian/menstrual cycle. Kenegsberg,*J. of Clin. Endo. and Met.*, Vol. 74, No. 1, p. 12, and may also play a role in the regulation of penile vascular tone in man, Lau et al., *Asia Pacific J. of Pharm.*, 1991, 6:287–292 and Tejada et al., *J. Amer. Physio. Soc.* 1991, H1078–H1085. Endothelin also mediates a potent contraction of human prostatic smooth muscle, Langenstroer et al., *J. Urology*, Vol. 149, p. 495–499.

Thus, endothelin receptor antagonists would offer a unique approach toward the pharmacotherapy of hypertension, acute and chronic renal failure, ischemia induced renal failure, sepsis-endotoxin induced renal failure, prophylaxis and/or treatment of radio-contrast induced renal failure, acute and chronic cyclosporin induced renal failure, cerebrovascular disease, cerebrovascular spasm, myocardial ischemia, angina, congestive heart failure, acute coronary syndrome, myocardial salvage, unstable angina, asthma, primary pulmonary hypertension, pulmonary hypertension secondary to intrinsic pulmonary disease, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, diabetic retinopathy, retinopathy, diabetic nephropathy, diabetic macrovascular disease, atherosclerosis, preclampsia of pregnancy, bone remodeling, kidney transplant, male contraceptives, infertility and priaprism and benign prostatic hypertrophy.

SUMMARY OF THE INVENTION

This invention comprises compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, benign prostatic hypertrophy, pulmonary hypertension, migraine, stroke, cerebrovascular vasospasm, myocardial ischemia, angina, congestive heart failure, atherosclerosis, diabetic nephropathy, diabetic retinopathy, retinopathy, diabetic macrovascular disease, atherosclerosis and as an adjunct in angioplasty for prevention of restenosis.

This invention further constitutes a method for antagonizing endothelin receptors in an animal, including humans, which comprises administering to an animal in need thereof an effective amount of a compound of Formula (I).

This invention also constitutes intermediates represented by Formula (II). In a further aspect the present invention provides a process for the preparation of a compound of Formula (I).

DETAILED DESCRIPTION OF THE INVENTION

The compounds of this invention are represented by structural Formula (I):

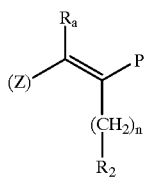

(I)

wherein Z is

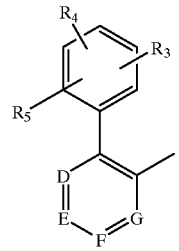

wherein D, E, F and G may be N, or $CR_1$ provided no more than three are nitrogens;

P is tetrazol-5-yl, $CO_2R_6$ or $C(O)N(R_6)S(O)_qR_{10}$;

$R_a$ is hydrogen or $C_{1-6}$alkyl;

$R_1$ is independently hydrogen, Ar or $C_{1-6}$alkyl, or $C_{1-6}$alkoxy;

$R_2$ is Ar, $C_{1-8}$alkyl, $C(O)R_{14}$ or

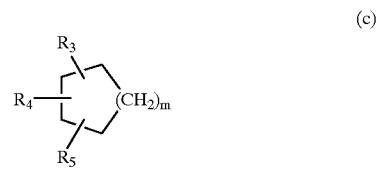

(c)

$R_3$ and $R_5$ are independently $R_{13}OH$, $C_{1-8}$alkoxy, $S(O)_qR_{11}$, $N(R_6)_2$, $NO_2$, Br, F, I, Cl, $CF_3$, $NHCOR_6R_{13}CO_2R_7$, —X—$R_9$—Y, —X(C($R_6$)$_2$)$OR_6$, —(CH$_2$)$_m$X'$R_8$ or —X(CH$_2$)$_n R_8$ wherein each methylene group within —X(CH$_2$)$_n R_8$ may be unsubstituted or substituted by one or two —(CH$_2$)$_n$Ar groups;

$R_4$ is independently $R_{11}$, OH, $C_{1-5}$alkoxy, $S(O)_qR_{11}$, $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen. $C_{1-10}$alkyl $C_{2-10}$alkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_n$Ar;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_m C(O)N(R_6)_2$, $C(R_{11})_2 N(R_7)_2$, $C(O)N(R_6)_2$, $NR_7C(O)NR_7SO_2R_{11}$, $OR_6$, or tetrazole which is substituted or unsubstituted by $C_{1-6}$alkyl;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one of more OH $N(R_6)_2$, COOH or halogen;

$R_{10}$ is independently $C_{1-10}$ alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$ alkylidene, $C_{2-10}$alkenylene, all of which may be unsubstituted or substituted by one or more OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently $C_{1-6}$alkyl or phenyl substituted by one or two $C_{1-6}$alkyl, OH, $C_{1-5}$alkoxy, $S(O)_qR_6$, $N(R_6)_2$, Br, F, I, Cl, $CF_3$ or $NHCOR_6$;

X is independently $(CH_2)_n$, O, $NR_6$ or $S(O)_q$;

X' is independently O, $NR_6$ or $S(O)_q$; Y is independently $CH_3$ or $X(CH_2)_n Ar$;

Ar is independently:

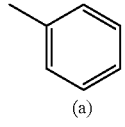

(a)

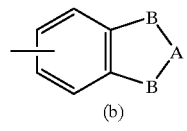

(b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $Z_1$ or $Z_2$ groups;

A is independently C=O, or $(C(R_6)_2)_m$;

B is independently —CH$_2$— or —O—;

$Z_1$ and $Z_2$ are independently hydrogen, $XR_6$, $C_{1-8}$alkyl, $(CH_2)_qCO_2R_6$, $C(O)N(R_6)_2$, CN, $(CH_2)_nOH$, $NO_2$, F, Cl, Br, I, $N(R_6)_2$, $NHC(O)R_6$, $O(CH_2)_mC(O)NR_aSO_2R_{15}$, $(CH_2)_m$ $OC(O)NR_aSO_2R_{15}$, $O(CH_2)_mNR_aC(O)NR_aSO_2R_{15}$ or tetrazolyl which may be substituted or unsubstituted by $C_{1-6}$akyl, $CF_3$ or $C(O)R_6$;

m is independently 1to 3;

n is independently 0 to 6;

q is independently 0, 1 or 2;

provided $R_3$ and $R_5$ are not O—O—$(CH_2)_nAr$ or O—O $R_6$; or a pharmaceutically acceptable salt thereof.

All alkyl, alkenyl, alkynyl and alkoxy groups may be straight or branched. Halogen may be Br, Cl, F or I.

The compounds of the present invention may contain one or more asymmetric carbon atoms and may exist in racemic and optically active form. All of these compounds and diastercoisomers are contemplated to be within the scope of the present invention.

Preferred compounds are those wherein:

is $CO_2R_6$; more preferably P is $CO_2H$.

$R_1$ is hydrogen, or $C_{1-6}$alkyl, or $C_{1-6}$ alkoxy.

$R_2$ is Ar, cyclohexyl or $C_{1-4}$alkyl. More preferably $R_2$ is a group Ar wherein Ar is a group (a) or (b). In said group (a) or (b) $Z_1$ and $Z_2$ are independently hydrogen, $CO_2R_6$, $(CH_2)_nOH$, $C_{1-4}$alkyl or $C_{1-6}$ alkoxy, e.g. methoxy; A is preferably $CH_2$, one or both Bs are preferably O.

$R_3$ and $R_5$ are independently hydrogen, $CO_2R_6$, OH, $C_{1-8}$alkoxy, $C_{1-8}$alkyl, $N(R_6)_2$, $NO_2$, Br, F, Cl, I, $R_{13}CO_2R_7$, $X(CH_2)_nR_8$, $(CH_2)_mX'R_8$, or $X(C(R_6)_2)_mOR_6$;

In the context of the group $R_3$ and $R_5$ preferably do not represent hydrogen. In particular in the group $R_3$ preferably represents Br, Cl, $C_{1-8}$alkoxy e.g, methoxy; $X(CH_2)_nR_8$, wherein X preferably represents O, n is 0, 1, or 2, and $R_8$ is preferably selected from:

$CO_2R_6$ wherein $R_6$ is preferably hydrogen;

$OR_6$ wherein $R_6$ is preferably H;

tetrazolyl optionally substituted by $C_{1-8}$alkyl e.g. ethyl;

$CONR_7SO_2R_{11}$ wherein $R_7$ is H or $C_{1-8}$alkyl e.g. methyl, $R_{11}$ preferably is $C_{1-8}$alkyl (e.g, methyl, isopryl, or t-butyl) or phenyl optionally substituted by Br, Cl, F, C $_{1-8}$alkyl e.g, methyl;

or $R_8$ is phenyl or pyridyl substituted by one or more Br, Cl, $CO_2H$, $CH_2OH$.

$R_5$ is $C_{1-8}$alkoxy e.g. methoxy, or $N(R_6)_2$ wherein $R_6$ preferably is H or methyl.

$R_4$ is hydrogen, OH, $C_{1-5}$alkoxy, $N(R_6)_2$, Br, F, Cl, I, $NHCOCH_3$, or $S(O)_q$ $C_{1-5}$alkyl wherein the $C_{1-5}$alkyl may be unsubstituted or substituted by OH, methoxy or halogen. $R_4$ is more preferably hydrogen;

$R_6$ is hydrogen or $C_{1-8}$alkyl e.g. methyl and ethyl;

$R_7$ is hydrogen, $C_{1-10}$ alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_nAr$, When $R_7$ is $(CH_2)_nAr$, n is preferably zero or 1 and Ar is preferably phenyl substituted or unsubstiruted by halogen or $C_{1-5}$ alkoxy.

$R_{11}$ is hydrogen, phenyl, pyridyl wherein the phenyl and pyridyl may be substituted or unsubstituted by one or two $C_{1-6}$alkyl groups, $C_{1-8}$alkyl, $C_{2-8}$alkenyl, $C_{2-8}$alkynyl, all of which may be substituted or unsubstituted by one or more OH, $CH_2OH$, $N(R_6)_2$, or halogen;

$R_{12}$ is hydrogen or $C_{1-6}$alkyl.

$R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen; and D, E, F and G are N, or $CR_1$ provided no more than two are nitrogens.

Preferred compounds are:

E-3-{5-[(2-cboxyphenyl)methoxy-4-methoxy]phenyl-6-n-propoxypyrmid-4yl]-2-}2-methoxy-4,5-methylenedioxybenzyl]-prop-2-enoic acid.

E-3-[4-[2-(2-Hydroxymethylphenyl)methoxy-4-methoxy]phenyl-5-propoxy-pyrdin-3-yl]-2-[2-methoxy-4,5-methylenedioxybenzyl]prop-2-enoic acid E-3-[4-[2-(2-Carboxyphenyl)methoxy-4-methoxy]phenyl-5-propoxy-pyridin-3-yl]-2-[2-methoxy4,5-methylenedioxybenzyl]prop-2-enoic acid E-3-[2-[(2-Hydroxymethylphenyl)methoxy-4-methoxyphenyl]-pyridin-3-yl]-2-[2-methoxy-4,5-methylenedioxybenzyl]prop-2-enoic acid E-3-(6-n-Propoxy-5-[2-(2-carboxyphenyl)methoxy-4-methoxyl]phenylpyrimid-4-yl]-2-[2-methoxy-4,5-methylenedioxybenzyl]-2-propenoic acid potassium salt The present invention provides compounds of Formula (I).

In a further aspect the present invention provides a process for the preparation of a compound of formula (I) comprising:

(a) to prepare a compound of formula (I), reaction of a compound of formula (II):

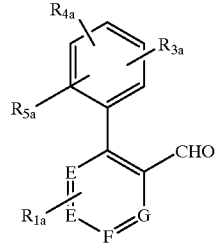

Formula (II)

wherein $R_{3a}$, $R_{4a}$ and $R_{5a}$ represent the groups $R_3$, $R_4$ and $R_5$ as defined for Formula (I) hereinabove, or a protected form or precursor thereof and $R_{1a}$ represents a group $R_1$ as defined for Formula (I) hereinabove, or a protected form or precursor thereof);

with a compound of Formula (III):

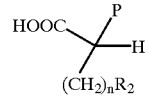

Formula (III)

wherein $R_2$ and P are as defined for formula (I) hereinabove and n is 0 to 5; followed if necessary or desired by:

(b) functional group interconversion of a compound of formula (I) into a different compound of formula (I) e.g.
  (i) when formula (I) contains an ester group e.g. $CO_2R_6$, conversion to a corresponding compound wherein $R_6$ represents hydrogen;
  (ii) when formula (I) contains a hydroxy group (e.g. in $R_3$, $R_4$ or $R_5$) conversion to a different group, eg a group $O(CH_2)Ar$ where Ar is as previously defined, by methods well known in the art; and/or
(c) salt formation.

Process (a) may be effected using standard procedures for the condensation of an aldehyde with an acidic CH group. Thus, for example, the reaction may be effected in a solvent such as benzene, using reflux conditions and a Dean-Stark trap, or heating in the presence of pyridine and acetic acid.

Conversion of an ester of formula (I) into an acid may be carried out using conventional deprotection techniques e.g. hydrolysis.

An aldehyde of formula (II) may be prepared from a compound of formula (IV):

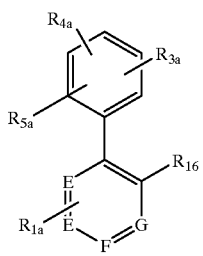

Formula (IV)

wherein $R_{3a}$, $R_{4a}$ or $R_{5a}$ and $R_{1a}$ are as defined above for formula (II) and $R_{16}$ is a group convertible to —CHO, such as an alcohol —$CH_2OH$ or 4,4-dimethyl-2-oxazoline; or a protected form or precursor thereof.

Conversion of $R_{16}$ may be effected by standard methods; for example an oxazoline group may be alkylated with iodomethane followed by reduction with sodium borohydride and hydrolysis and oxidation of an alcohol may be effected using activated manganese dioxide.

A compound of formula (IV) may be prepared by coupling appropriately substituted phenyl derivatives according to processes well known in the art. Thus for example a compound of formula (V);

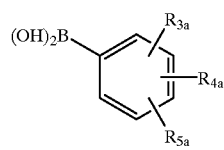

Formula (V)

wherein $R_{3a}$, $R_{4a}$ or $R_{5a}$ are as hereinbefore defined, may be coupled with a compound of formula (VI):

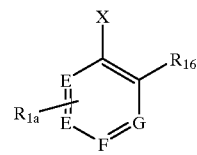

Formula (VI)

wherein X' represents Cl, Br, or I; and $R_{16}$ and $R_{1a}$ are as hereinbefore defined or a protected form or precursor thereof, in the presence of Pd $(PPh_3)_4$, or other Pd ligands such as bis(1,4 diphenylphosphino)butane or bis(diphenyl)phosphinoferrocene.

A compound of formula (V) may be prepared by reaction of a corresponding organometallic derivative (eg lithium or Grignard) with a trialkyl borate followed by hydrolysis.

A compound of formula (VI) may be prepared by reacting a compound of formula (VII):

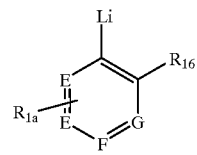

Formula (IX)

wherein $R_{1a}$ and $R_{16}$ are as hereinbefor defined, with iodine or alternatively by direct halogenation.

It will be appreciated by those skilled in the art that the substitutents $R_1$, $R_3$, $R_4$, and $R_5$ may be introduced at any appropriate stage of the synthesis, preferably at an early stage, using methods well known in the art. In some of the reactions depicted above, particularly those in the early stages of the overall synthesis, one or more of the substitutents $R_1$, $R_3$, $R_4$, and $R_5$ may therefore represent a precursor for the eventual substituent. A precursor for any of the substitutents $R_1$, $R_3$, $R_4$, and $R_5$ means a group which may be derivauzed or converted into the desired group $R_1$, $R_3$, $R_4$, and $R_5$. It will be further appreciated that it may be necessary or desirable to protect certain of these substitutents(or their precursors) at various stages in the reaction sequence. Suitable precursors and protecting groups are well known to those skilled in the art, as are methods for their conversion or removal respectively.

Thus for example, wherein $R_3$ represents a substituted benzyloxy group, this may be introduced subsequent to the coupling reaction between compounds (II) and (III), the earlier preparative stages being effected with intermediates wherein $R_3$ represents hydroxy, which may be protected as necessary, for example as a methoxymethyl ether. Thus when, $R_3$ or $R_4$, represents a group $O(CH_2)_nCO_2R_6$ it may be formed from a precursor hydroxy group by reaction with an appropriate halo ester e.g. ethyl bromoacetate.

In order to use a compound of the Formula (I) or a pharmaceutically acceptable salt thereof for the treatment of humans and other mammals it is normally formulated in accordance with standard pharmaceutical practice as a pharmaceutical composition.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sublingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (I) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

Binding Assay

A) CHO cell membrane preparation.

CHO cells stably transfected with human $ET_A$ and $ET_B$ receptors were grown in 245 mm×245 mm tissue culture plates in Dulbecco's modified Eagle's medium supplemented with 10% fetal. bovine serum The confluent cells were washed with Dulbecco's phosphate-buffered saline containing a protease inhibitor cocktail (5 mM EDTA, 0.5 mM PMSF, 5 ug/ml of leupeptin and 0.1 U/ml of aprotinin) and scraped in the same buffer. After centnfugation at 800×g, the cells were lysed by freezing in liquid nitrogen and thawing on ice followed by homogenization (30 times using a glass dounce homogenizer) in lysis buffer containing 20 mM Tris HCI, pH 7.5, and the protease inhibitor cocktail. After an initial centrifugation at 800×g for 10 min to remove unbroken cells and nuclei, the supernatants were centrifuged at 40.000×g for 15 min and the pellet was resuspended in 50 mM Tris HCI, pH 7.5, and 10 mM $MgCl_2$ and stored in small aliquots at −70° C. after freezing in liquid $N_2$. Protein was determined by using the BCA method and BSA as the standard.

(B) Binding studies.

[$^{125}$I]ET-1-binding to membranes prepared from CHO cells was performed following the procedure of Elshourbagy et al. (1993). Briefly, the assay was initiated in a 100 ul volume by adding 25 ul of [$^{125}$I]ET-1 (0.2–0.3 nM) in 0.05% BSA to membranes in the absence (total binding) or presence (nonspecific binding) of 100 nM unlabeled ET-1. The concentrations of membrane proteins were 0.5 and 0.05 ug per assay tube for $ET_A$ and $ET_B$ receptors, respectively. The incubations (30° C. 60 min) were stopped by dilution with cold buffer (20 mM Tris HCI, pH 7.6, and 10 mM $MgCl_2$) and filtering through Whatman GF/C filters (Clifton, N.J.) presoaked in 0.1% BSA. The filters were washed 3 times (5 ml each time) with the same buffer by using a Brandel cell harvester and were counted by using a gamma counter at 75% efficiency.

The following examples are illustrative and are not limiting of the compounds of this invention.

EXAMPLE 1

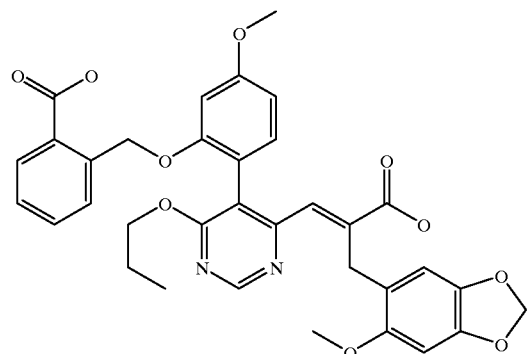

E-3-[6-n-Propoxy-5-[2-(2-carboxyphenyl)methoxy-4-methoxylphenylpyrimid-4-v1]2-[2-methoxy-4, 5-methylenedioxybenzyl-2-propenoic acid potassium salt a) 1-Methoxy-3,4methylenedioxybenzene To a solution of sesamol (10.0 g, 0.072 mol) in DMF (50 ml) was added sodium hydride (2.08 g, 0.087 mol) at room temperature under argon. After stirring for 1 h, the mixture was treated with iodometharc (13.5 ml. 0.216 mol) and stirred for another 18 h. Upon the removal of the solvent the residue was extracted with ethyl acetate and washed with water, dried (Na$_2$SO$_4$) and concentrated to afford the title compound as a dark brown oil (10.5 g, 96%).

b) 2-Methoxy-4,5-methylenedioxy benzaldehyde

To a solution of phosphorous oxychloride (3.0 ml. 0.033 mol) in DMF (10 ml) was added a solution of 1-methoxy-3,4-methylenedioxybenzene ( 2.0 g, 0.013 mol) in DMF (2 ml) at 0° C. After stirring at 60° C. for 18 h the mixture was cooled to 0° C. and then poured into water (500 ml). The precipitate was filtered and dried. The tide compound was collected as a yellow solid (2.20 g. 92%).

c) Diethyl 2-(2-methoxy-4,5-methylenedioxybenzyiiden)-malonate

A solution of the 2-methoxy-4,5-methylenedioxy benzaldehyde (16.0 g, 0.089 mol), diethyl malonate (15.0 ml, 0.090 mol), piperidine (4.4 ml, 0.044 mol) and acetic acid (2.5 ml, 0.045 mol) in benzene (75 ml) was stirred at reflux, equipped with a Dean-Stark apparatus, for 24 h. Upon removal of the solvent the crude residue was extracted with ethyl acetate and washed with 10% sodium carbonate solution, water, dried (Na$_2$SO$_4$). After removing the solvent, flash chromatography of the residue (silica gel, 25% ethyl acetate/hexane) provided the title compound as a yellow solid (26.0 g. 91%).

d) Diethyl 2-(2-methoxy-4,5-methylenedioxybenzyl)-malonate

To a solution of the diethyl 2-(2-methoxy-4,5-methylenedioxybenylidene)-malonate (23.4 g, 0.073 mol) in ethanol (100 ml) was added sodium borohydride (2.8 g, 0.073 mol) and the mixture was stiffed at rt for 5 h. The reaction was quenched with water and extracted with ethyl aceate (3×200 mL). The combined organic extracts were dried (Na$_2$SO$_4$) and evaporated to afford the title compound as an oil (20.3 g, 86%).

e) 2-Ethoxycarbonyl-3-(3,4-methylenedioxyphenyl) propanoic acid

To a solution of the diethyl 2-(2-methoxy-4,5-methylenedioxybenyl)-malonate (20.0 g, 0.066 mol) of in ethanol (50 ml) was added a solution of potassium hydroxide (3.5 g, 0.066 mol) in water (25 ml). The solution was stirred at reflux for 6 h. After concentrating the aqueous layer was washed with ether and acidified with concentrated HCl to pH 1 and extracted with ethyl acetate. The organic extracts were dried (Na$_2$SO$_4$) and concentrated to afford the title compound as a yellow solid (17.3 g, 89%).

f) 1-Bromo-2-methoxymethoxy-4-methoxybenzene

To a solution of 1-Bromo-2-hydroxy-4methoxybenzene (5.00 g. 24.60 mmol) in DMF was added 60% sodium hydride (1.97 g, 49.20 mmol) at 0° C. under argon. The mixture was allowed to stir at 0° C. for 15 minutes, then 90% bromomethyl methylether (4.10 g, 29.50 mmol) was added. After stirring for 1 h 0° C. the reaction was quenched with water. The mixture was extracted with ethyl acetate and the combined organic extracts were washed with brine and dried (Na$_2$SO$_4$). Removal of the solvent afforded the title compound as an oil (6.5 g, quantitative yield). $^1$H NMR (400 MHz, CDCl3) δ 7.41 (d. 2H), 6.76 (d, 1H), 6.47 (dd, 1H), 5.24 (s, 2H), 3.87 (s, 3H), 3.53 (s, 3H).

g) 2-Methoxymethoxy-4-methoxyphenyl boronic acid

To a solution of 1-Bromo-2-methoxymethoxy-4-methoxybenzene (6.10 g, 24.63 mmol) in THF (100 mL) was added 1.6M n-butyl lithium in hexane (15.4 mL, 24.63 rmnol) at −78° C. under argon. The reaction was allowed to stir at −78° C. for 1 h, then quenched with water and extracted with ethyl acetate. The organic extract was washed with brine and dried (Na2SO4). Removal of the solvent under reduced pressure afforded the tide compound as solid (4.50 g. 87%). $^1$H NMR (400 MHz, CDCl3) δ 7.76 (d, 1H), 6.72 (d. 1H), 6.63 (dd. 1H), 5.75 (s, 2H), 5.30 (s. 2H), 3.83 (s, 3H), 3.58 (s, 3H).

h) Ethyl 4-benzytoxyacetoacetate

To a stirred suspension of NaH (3 g, 0, mmol, 80% oil dispersion previously washed with hexanes), in THF (75 ml, distilled from Na) was added dropwise neat benzyl alcohol (10.3 g. 0.1 mmol) at rt. Sting was continued until H$_2$ evolution had ceased, then ethyl 4-chloroacetoacetate (8.23 g, 0.05 mmol) in THF (20 ml) was added dropwise to this solution in a cooling water bath. The reaction was stirred at rt overnight. The mixture was partitioned between ether and 1N HCl, the layers separated, and the aqueous further extracted with ether (×2). The combined ether extracts were washed twice with water and then brine and dried ( Na$_2$SO$_4$), filtered. and concentrated in vacuo to give 17.83 g crude product. Distillation (119–124° C., 0.2 mm Hg) afforded a yellow oil. ( 7.34 g. 62%)

i) 6-Benzyloxymethyl-4-hydroxy-pyrmidine

A solution of NaOCH$_3$ was prepared by adding Na (1.2 g, 51.82 mmol) to methanol (45 ml) at rt with stirring under argon. After H$_2$ evolution had ceased, formamidine acetate (2.31 g. 22.2 mmol) was added at 0° followed by dropwise addition of ethyl 4-benzyloxyacetoacetate (3.5 g, 14.81 mmol) and stirring was continued at rt for 3 d then at reflux temperature for 5 h. The methanol was removed under reduced pressure and the remaining yellow solid was partitioned between ether and water and the resulting ether extract discarded. Then aqueous layer was neutralized with acid and extracted with ether (×3). Concentration of the combined extracts afforded a crude solid which was triturated with hot ether to give white solid. (2.085 g, 65%)

j) 6-Benzyloxymethyl-4-hydroxy-5-iodo-pyrimidine

A solution of 6-benzyloxymethyl-4-hydroxy-pyrimidine (4.55 g, 20.87 mmol) and N-iodosuccinimide (5.165 g, 23 mmol) in chloroform (250 ml) was kept at reflux under argon for 2 h. The solution was washed with water, 0.5 N sodium thiosulfate, and brine. After drying (MgSO$_4$), filtration and concentration gave a white solid (6.56 g. 91%).

k) 6-Benzyloxymethyl-4-chloro-5-iodo-pyrimidine

A solution of 6-benzyioxymethyl-4-hydroxy-5-iodo-pyrimidine (6.56 g, 1.9 mmol) dissolved in phosphorus oxychloride (200 ml) was stirred at reflux for 20 min. The POCl$_3$ was removed under reduced pressure and the residue evaporated from toluene. The reddish residue was partitioned between ice-water and t-butyl methyl ether, then treated with NaHCO$_3$, and the layers separated, and the aqueous layer was further extracted (×2). The combined organic extracts were washed twice with 5% sodium bicarbonate solution and once with brine, and then dried (Na$_2$SO$_4$), filtered and concentrated under reduced pressure to give the crude product as a brown oil (6.64 g, 97%).

l) 6-Benzyloxymethyl-5-iodo-4-propoxy-pyrinmidine

A solution of sodium propoxide was prepared from NaH (0.573 g, 19.1 mmol, 80% oil dispersion) in n-propanol (150 ml) and 6-benzyloxymethyl-4-chloro-5-iodo-pyrimidine in n-propanol (40 ml) was added dropwise and the reaction kept at 40° for 20 min. The propanol was removed under reduced pressure and the residue partitioned between t-butyl methyl ether and water. The layers were separated, and the aqueous further extracted (×3). The combined organic extracts were washed twice with water, 5% sodium bicarbonate solution, and brine, and then dried (MgSO$_4$), filtered and concentrated under reduced pressure. Silica gel chromatography (60%ether/hexanes) afforded a yellow oil. (5.00 g, 72%)

m) 6-Benzyloxymethyl-5(2-methoxymethoxy-4-methoxyphenyl)-4propoxy-pyrimidine

To a solution of 2-methoxymethoxy-4-methoxyphenyl boronic acid (2.89 g. 13.65 mmol) in MeOH (8–10 ml) and 6-benzyloxymethyl-5-iodo-4-propoxy-pyrirnidine (5 g. 13 mmol) in toluene (75 ml) was added an aqueous solution of 2 M sodium carbonate (14 ml) followed by Tetrakis (triphenylphosphine)palladium (0) (1.25 g, 1.08 mmol). The reaction was allowed to stir at 90–95° for 18 h. The mixture was cooled to room temperature then diluted with ethyl acetate, washed with water, sat'd $NH_4Cl$, 5% $NaHCO_3$ solution. brine and dried ($MgSO_4$). After removing the solvent, flash chromatography of the residue (silica gel, 1:1 t-butyl methyl ether/hexane) provided the title compound as a solid (3.41 g, 62%).

n) 6-Hydroxymethyl-5-(2-methoxymethoxy-4-methoxyphenyl)-4-propoxy-pyrimidine

A solution of 6-benzyloxymethyl-5-(2-methoxymethoxy-4-methoxyphenyl)4-propoxy-pyrimidine (3.41 g, 8.04 mmol), cyclohexene (35 ml), $Pd(OH)_2$ (3.4 g) and ammonium formate (3.4 g) in ethanol (100 ml) was kept at reflux for 3 d. After cooling the mixture was filtered through celite and concentrated to an oil. (2.42 g. 90%).

o) 6-formyl-5-(2-methoxymethoxy-4-methoxyphenyl)-4-propoxy-pyrimidine

A solution of 6-hydroxymethyl-5-(2-methoxymethoxy-4-methoxyphenyl)4-propoxy-pyrimidine in $CH_2Cl_2$ was treated with $MnO_2$ and stirred vigorously for 24 h. The mixture was filtered through celite and concentrated to afford the tide compound (1.48 g, 62%).

p) (E) Ethyl 3-[5-(2-methoxymethoxy-4-methoxy)phenyl-6-n-propoxypyrimid-4yl[-2-[2-methoxy-4,5-methylenedioxybenzyl]-2-propenoate.

A mixture of the aldehyde of Example 1(p), (1.48 g, 5.25 mmol), 2-ethoxycarbonyl-3-(3,4-methylenedioxyphenyl) propanoic acid (2.34 g. 7.88 mmol), piperidine (223 mg, 0.26 ml, 2.7 mmol) and acetic acid (0. 17 ml) in benzene (50 ml) was stirred at reflux under argon using a Dean-Stark trap. After 18 hours, the benzene was removed in vacuo and the residue partitioned between t-butyl methyl ether and water. The layers were separated, and the aqueous further extracted (×3). The combined organic extracts were washed twice with water, 5% sodium bicarbonate solution, sat'd ammonium chloride, and brine, then dried ($MgSO_4$), filtered and concentrated under reduced pressure. Silica gel chromatography (50% ether/hexanes) afforded the title compound as an oil. (1.048 g, 42%)

q) (E) Ethyl 3-[5-(2-hyroxy-4-methoxy)pheny-6-n-propoxypyrimid-4yl]-2-[2-methoxy-4,5-methyienedioxybenzyl]-2-propenoate.

(E) Ethyl 3-]5-(2-methoxymethoxy-4-methoxy)phenyl-6-n-propoxypyrmid-4yl-2-[2-methoxy-4,5-methylenedioxybenzyl]-2-propenoate (1.04 g, 1.84 mmol) in methanol (30 ml) with 30 drops of conc. HCl was stirred at reflux for 2 h. After cooling the methanol was removed in vacuo and residue partitioned between ethyl acetate and 5% $NaHCO_3$. The combined extracts (×3) were washed with water, brine, dried ($Na_2SO_4$), and concentrated to give a the title compound as pale yellow foam after pumping under high vacuum (0.90 g, 94%).

r) Methyl-2-bromomethyl)benzoate

To a solution of methyl-2-methylbenzoate (3.00 g, 20.0 mmol) in carbon tetrachloride (15 ml) was added N-bromosuccinimide (3.55 g. 20.00 mmol). The reaction was allowed to stir at reflux for 3 h. The mixture was cooled and then partioned between t-butyl methyl ether and 5% $NaHCO_3$. The combined organic extracts (×3) were washed with water, brine, and dried ($MgSO_4$). Removal of the solvent under reduced pressure afforded the title compound as a white solid (4.60 g, quantitative yield). $^1H$ NMR (400 MHz. $CDCl_{13}$) δ 7.98 (d, 1H), 7.54–7.35 (mm, 3H), 4.98 (s, 2H), 3.98 (s. 3H)

s) (E) Ethyl 3-{5-[2-(2-methoxycarbonylphenyl)methoxy-4-methoxy]phenyl-6-n-propoxypyrimid-4yl}-2-[2-methoxy-4,5-methylenedioxybenzyl]-2-propenoate.

In a flame dried flask under argon was placed sodium hydride (11 mg, 0.36 mmol, 80% oil dispersion washed with ligroin). To this was added dry DMF (1 ml) and then a solution of phenol of description (j) (174 mg, 0.33 mmol) in DMF (2 ml). The yellow-green colored phenolic solution turned deep red. After 5 min at rt, methyl-2-bromomethylbenzoate (127 mg, 0.55 mmol) was added and the reaction stirred for an additional 10 min. The mixture was partitioned between t-butyl methyl ether and 5% sodium bicarbonate solution. The layers were separated, and the aqueous further extracted (×3). The combined organic extracts were washed twice with water, brine, then dried ($MgSO_4$), filtered and concentrated under reduced pressure to give a brown oil (264 mg). Silica gel chromatography (25% to 50% t-butyl methyl ether/hexanes) afforded the title compound as an oil (130 mg, 58%) along with the Z isomer: (20 mg, 9%).

t) E-3-[6-n-Propoxy-5-[2-(2-carboxyphenyi)methoxy-4-methoxy]phenylpyrimid-4-yl]2-[2-methoxy-4,5-methylenedioxybenzyl]-2-propenoic acid potassium salt To a solution of (E) ethyl 3-{5-[2-(2-methoxycarbonylphenyl)methoxy-4-methoxy]phenyl-6-n-propoxypyrimid-4yl)-2-[2-methoxy-4,5-methylenedioxybenzyl]-2-propenoate (0.125 g, 0.186 mmol) in propanol (2 mL) was added 3N potassium hydroxide (2 mL). The reaction was allowed to stir at 95° for 4 h. The mixture was cooled and the propanol removed in vacuo, then the residue was acidified with 0.5N $NaH_2PO_4$ to a pH of 4.5. The mixture was extracted with t-butyl methyl ether (3×50 mL), and the combined organic extracts were washed with brine and dried ($Na_2SO_4$). Removal of the solvent under reduced pressure afforded the title compound as a gum (0.128 g). Chromatography (silica gel, 85:15:1.5 $CHCl_3$:MeOH:$H_2O$) afforded the title compound as a pale yellow solid (99 mg, 85%). $^1H$ NMR (400 MHz, $CDCl_3$ with trace of TFA) δ 8.95(s. 1H), 8.04 (d, 1H, J=8 Hz), 7.65 (s, 1H), 7.51 (t, 1H),7.40–7.35 (m, 2H), 7.01 (d, J=8 Hz, 1H), 6.55 (d, J=8 Hz), 1H), 6.47 (s, 1H), 6.38 (s, 1H), 6.33 (s, 1H), 5.83 (d, J=5.6 Hz, 2H), 5.48 (JAB=15 Hz, Δδ=32 Hz, 2H), 4.5 (m, 2H), 3.77 (s, 3H), 3.48 (s, 3H), 3.33 (JAB=19 Hz, Δδ=38 Hz, 2H), 1.73 (sextet, 2H), 0.93 (t, J=7.4 Hz, 3H); MS(ESP) m/e 629 [M+H]$^+$; MS(ESN) m/e 627 [M–H]$^-$; mp: 201–202° C.; Anal. ($C_{34}H_{31}N_2O_{10}K$) calcd. C, 61.23; H, 4.69; N, 4.20: found. C, 61.09: H, 4.45; N, 4.13.

u) E-3-[6-n-Propoxy-5-[2-(2-carboxyphenyl)methoxy-4-methoxy]phenylpyrimid-4-yl]2-[2-methoxy-4,5-methylenedioxybenzyl]-2-propenoic acid Following the same procedure as in Example (1)(t) except that in the work-up the aqueous phase was acidified to pH 3 with $H_3PO_4$. The title compound was recrystalized from t-butyl methyl ether as a white solid. $^1H$ NMR (400 MHz, $CD_3CN$) δ 8.85(s, 1H), 7.95 (d, 1H, J=7.4 Hz), 7.35 (s, 1H), 7.40–7.29 (m, 2H), 7.25 (d, J=7.4 Hz, 1H) 7.01 (d. J=8.4 Hz, 1H), 6.61 (d, J=8.4 Hz, 1H), 6.57 (s, 1H), 6.51 (s, 1H), 6.46 (s, 1H), 5.80 (s, 2H), 5.39 (s, 2H), 4.24 (m, 2H), 4.00 (JAB=14.7 Hz, Δδ=75 Hz, 2H), 3.80 (s, 3H), 3.59 (s, 3H), 1.57 (sextet, 2H), 0.79 (t, j=7.4 Hz, 3H); MS(ESP) m/e 629 [M+H]$^+$; MS(ESN) m/e 627 [M–H]$^-$; mp: 198–200° C.; Anal. ($C_{34}H_{31}N_2O_{10}$) calcd. C, 64.96; H, 5.13; N, 4.46: found. C, 61.64; H. 501; N, 4.32.

EXAMPLE 2

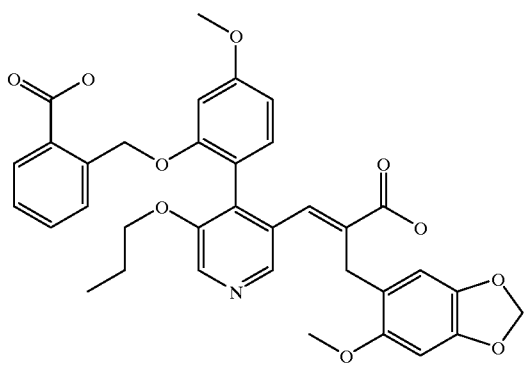

E-3-[4-[2-(2-Carboxypenyl)methoxy-4-methoxyphenyl-5-propoxy-pyridin-3-y1]-2-[2-methoxy-4, 5-methylenedioxybenzyl]prop-2-enoic acid a) Methyl-5-diethyicarbonyloxynicotinate To a stirred solution of methyl-5-hydroxynicotinate (5 g, 32.65 mmol), triethylamine (9 ml, 64.6 mmol), 4-dimethylaminopyridine (200 mg, 1.64 mmol) in methylene chloride (50 ml) under argon was added dimethylcarbamoyl chloride (4.15 ml, 32.99 mmol) at rt and the reaction was st overnight at rt. The mixture was diluted with methylene chloride and washed with 5% NaHCO$_3$, water (×2), brine, dried (MgSO$_4$), and concentrated to afford the title compound as an oil (9.3 g, quantitative).

b) 3-Diethylcarbonyloxy-5-hydroxymethyl-pyridine

At 0° an ethereal solution of 1M lithium aluminum hydride (14 ml, 14 mmol) was added dropwise to a stirred solution of crude methyl-5-diethylcarbonyloxynicotinate (4.06 g, 16.11 mmol) in ether (60 ml) under argon. A pale yellow precipitate formed upon adddition. Basic hydrolysis with water, 10% NaOH and water (0.55 ml, 0.825 ml and 1.6 ml respectively) gave a flocculent precipitate which was filtered and washed with t-butyl methyl ether and discarded. The filtrate was dried (MgSO$_4$) and concentrated and the resulting oil (2.66 g) was flash chromatographed (silica gel, 70% –100% t-butyl methyl ether/hexanes) to afford the title compound as a colorless oil. (2.03 g, 56%).

c) 3-Diethylcarbonyloxy-5-hydroxymethyl-4-iodo-pyridine

At −78° under argon was added dropwise over 30 min a solution of 1.3 M sec-BuLi (1.62 ml, 2.1 mmol) to a stirred solution of 5-diethylcarbonyloxy-3-hydroxymethyl-pyridine in dry THF (224 mg, 1 mmol). After stirring 15 min at −78°, diiodoethane was added (563 mg, 2.1 mmol) in dry THF (5 ml) and the reaction was stirred for 1 hr at −78°, then allowed to warm to rt. The mixture was partitioned between t-butyl methyl ether and 5% sodium bicarbonate solution . The layers were separated, and the aqueous further extracted (×3). The combined organic extracts were washed with 15% sodium thiosulfate, water, brine, then dried (MgSO$_4$), filtered and concentrated under reduced pressure to give a reddish oil (327 mg). Silica gel chromatography (70%–100% t-butyl methyl ether/hexanes) afforded the title compound as an oil which solidified upon standing to a white solid (109 mg, 31%).

d) 3-Diethylcarbonyloxy-5-hydroxymethyl-4-(2-methoxymethoxy-4-methoxyphenyl)- pyridine A mixture of palladium acetate (35 mg, 0.157 mmol) and bis(1,4 diphenylphosphino)butane (74 mg, 0.173 mmol) in degassed dimethoxyethane (64 ml) was heated gently for 30–60 seconds, and to this red solution was added 5-Diethylcarbonyloxy-3-hydroxymethyl-4-iodo-pynrdine (790 mg, 2.25 mmol), solid NaHCO$_3$, 2-methoxymethoxy-4-methoxyphenyl boronic acid (574 mg, 2.7 mmol), and degassed water (1.6 ml) under argon in a sealed tube. The reaction was stir at 90–95° for 18 h. The mixture was cooled to room temperature then diluted with t-butyl methyl ether, washed with water, 5% NaHCO$_3$ solution, brine and dried (Na$_2$SO$_4$). After removing the solvent, flash chromatography of the residue (silica gel, 5% methanol/methylene chloride) provided the title compound as a solid (741 mg, 84%).

e) 3-hydroxy-5-hydroxymethyl-4-(2-methoxymethoxy-4-methoxyphenyl)-pynridine

A mixture of 3-diethylcarbonyloxy-5-hydroxymethyl-4-(2-methoxymethoxy-4-metboxyphenyl)- pyridine (790 mg, 2.02 mmol) and 2.5 N NaOH (30 ml) in methanol (30 ml) were stirred at reflux for 18 h. The methanol was removed in vacuo, the aqueous residue acidified to pH 7.4, and extracted with ethyl acetate (×3). The combined organic extracts were dried (Na$_2$SO$_4$) and concentrated to afford the title compound as a white glass (550 mg, 94%)

f) 5-hydroxymethyl-4-(2-methoxymethoxy-4-methoxyphenyl)-3-propoxy-pyridine

A mirxture of 3-hydroxy-5-hydroxymethyl-4-(2-methoxymethoxy-4-methoxy-phenyl)-pyridine (550 mg, 1.89 mmol), iodopropane (0.210 ml, 2.15 mmol), potassium carbonate (3 g) in dry DMF (70 ml) was stirred overnight at rt. The mixture was dissolved in water and extracted with a 1:1 hexane:t-butyl methyl ether solution (×3) and washed with brine, dried (Na$_2$SO$_4$), and concentrated to afford the title compound as a greenish oil. (527 mg, 84%)

g) E-3-[4-(2-(2-Carboxyphenyl)methoxy-4-methoxy]phenyl-5-propoxy-pyridin-3-yl]-2-(2-methoxy-4,5-methylenedioxybenzyl]prop-2-enoic acid Following the procedure of Example 1(o)-1(u) except substituting 5-hydroxymethyl-4-(2-methoxymethoxy-4-methoxyphenyl)-3-propoxy-pyridine for 6-hydroxymethyl-5-(2-methoxymethoxy-4-methoxyphenyl)-4-propoxy-pyrimidine, the title compound was prepared as a tan solid (138 mg, 25% ). (400 MHz, CDCl$_3$) δ 8.32 (s, 1H), 8.12 (d. 1H, J=7.6 Hz), 8.06 (s, 1H), 7.56 (s, 1H), 7.48 (t. 1H), 7.40–7.35 (m, 2H), 7.12 (d, J=8.4 Hz, 1H), 6.67 (s, 1H), 6.63 (d, J=8.5 Hz, 1H), 6.44 (s, 1H), 6.42 (s, 1H), 5.83 (d, J$_{AB}$=2 Hz, 2H), 5.42 (s, 2H), 3.9 (m, 2H), 3.88 (s, 3H), 3.67 (s, 3H), 3.07 J$_{AB}$=16.7 Hz, Δδ=87 Hz, 2H), 1.70 (sextet, 2H), 0.92 (t, J=7.4 Hz, 3H); MS(ESP) m/e 628 [M+H]$^+$; MS(ESN) m/e 626 [M−H]$^-$; mp: 111.5–116° C.; Anal. (C$_{35}$H$_{33}$NO$_{10}$.0.5 H$_2$O) calcd. C, 66.03; H, 5.38; N, 2.20: found. C, 65.84; H, 5.25; N, 2.13; HPLC t$_{R9.87}$ min, 20.02 min (Bakerbond Chiracel OC®; 25 cm ×4.6 mm; hexane:ethanol, 85% with.1%TFA; 1.0 mL/min; UV detection at 245 nm).

EXAMPLE 3

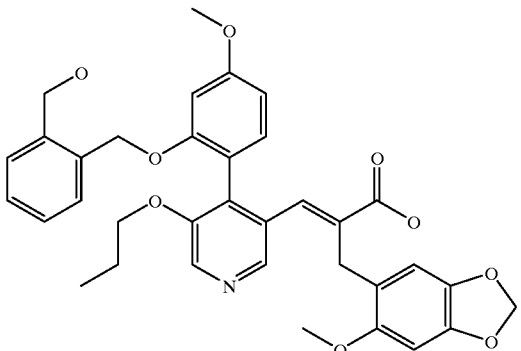

E-3-[4-[2-(2-Hyroxymethylphenyl)methoxy-4-methoxyphenyl-5-propoxy-pyridin-3-y1]-2-[2-methoxy-4, 5-methylenedioxybenzyl]prop-2-enoic acid
mp 88.0 - 90.0

17 a) 2-Hydroxymethylbenzyl bromide

A mixture of 1,2 benzenedimethanol (1.41 g, 10 mmol), carbontetrabromide (3.648 g, 11 mmol), triphenylphosphine (2.885 g, 11 mmol) in dry methylene chloride (50 ml) was stirred at rt over 2 days under argon. The solvent was removed under reduced pressure and the residue chomatographed (flash silica gel, 1:1 t-butyl methyl ether: hexanes) to afford the title compound as a white solid. (0.99 g, 49%)

b) E-3-[4-[2-(2-Hydroxymethylphenyl)methoxy-4-methoxy]phenyl-5-propoxy-pyridin-3-yl]-2-[2-methoxy-4,5-methylenedioxybenzyl]prop-2-enoic acid Following the procedure of Example 1(o)-1(v) except substituting 5-hydroxymethyl-4-(2-methoxymethoxy-4-methoxyphenyl)-3-propoxy-pyridine for 6-hydroxymethyl-5-(2-methoxymethoxy-4-methoxyphenyl)-4-propoxy-pyrinidine and 2-hydroxy-methylbenzyl bromide for methyl-2-bromomethylbenzoate the tide compound was prepared. (77 mg, 28%) (400 MHz, CDCl$_3$) δ 8.22 (s, 1H), 8.10 (s, 1H), 7.50 (s. 1H), 7.34–7.15 (m, 4H), 6.94 (d, J=8.4 Hz, 1H), 6.65 (s, 1H), 6.57 (d, J=8.5 Hz, 1H), 6.44 (s. 1H), 6.43 (s, 1H), 5.84 (s, 2H), 5.05 (dd, J$_{AB}$=11.8 Hz, Δδ=29 Hz, 2H), 4.51 (dd, 2H) 3.9–3.8 (m, 2H), 3.85 (s, 3H), 3.64 (s, 3H), 3.47 (J$_{AB}$=16.4 Hz, Δδ=51.1 Hz, 2H), 1.59 (sextet, 2H), 0.81 (t, J=7.4 Hz, 3H); MS(ESP) m/e 614 [M+H]$^+$; MS(ESN) m/e 612 [M–H]$^-$; mp: 88.0–90.0° C.; Anal. (C$_{35}$H$_{35}$NO$_9$.0.75 H$_2$O) calcd. C, 67.02; H, 5.87; N, 2.23: found. C, 67.09; H, 5.86; N, 2.30; HPLC t$_R$ 11.77 min, 20.90 min (Bakerbond Chiracel OC®; 25 cm×4.6 mm; hexane:ethanol, 85% with 0.1% TFA; 1.0 mL/min; UV detection at 245 nm).

18 b) 3-Formyl-4-(2-methoxymethoxy-4-methoxyphenyl)-pyridine

Following the procedure of Example 2(d) except substituting 4-chloro-3-formyl-pyridine for 5-Diethylcarbonyloxy-3-hydroxymethyl-4-iodo-pyridine, the title compound was prepared as a white solid.(52 mg, 95%)

c) E-3-[4-[2-(2-Carboxyphenyl)methoxy-4-methoxy]phenylpyridin-3-yl]-2-[2-methoxy-4,5-methylenedioxybenzyl]prop-2-enoic acid Following the procedure of Example 1(p)-1(u) except substituting 3-formyl-4-(2-methoxymethoxy-4-methoxyphenyl)-pyridine for 6-formyl-5-(2-methoxymethoxy-4-methoxyphenyl)-4-propoxy-pyrimidine the title compound was prepared. (89 mg, 42%) (400 MHz, CDCl$_3$) δ 8.51 (d, J=5.1, 1H), 8.36 (s, 1H), 7.90 (d, J=7.6, 1H), 7.51 (s, 1H), 7.50–7.36 (m, 4H), 7.28 (d, J=8.0 Hz, 1H), 7.06 (d, J=8.3 Hz, 1H), 6.70 (s, 1H), 6.64 (d, J=8.5 Hz, 1H), 6.60 (s, 1H), 6.31 (s, 1H), 5.90 (s, 2H), 5.37 (s, 2H), 3.79 (s, 3H), 3.60 (s, 3H), 3.38 (s, 2H); MS(ESP) m/e 570 [M+H]$^+$; MS(ESN) m/e 568 [M–H]$^-$, mp: 211–212° C.; Anal. (C$_{32}$H$_{27}$NO$_9$.0.375 H$_2$O) calcd. C, 66.69; H, 4.85; N, 2.43: found. C, 66.64; H, 4.87; N, 2.27; HPLC t$_R$ 16.25 min, (Bakerbond Chiracel OC®; 25 cm×4.6 mm; hexane:ethanol, 85% with 0.1% TFA; 1.0 mL/min; UV detection at 245 nm).

EXAMPLE 4

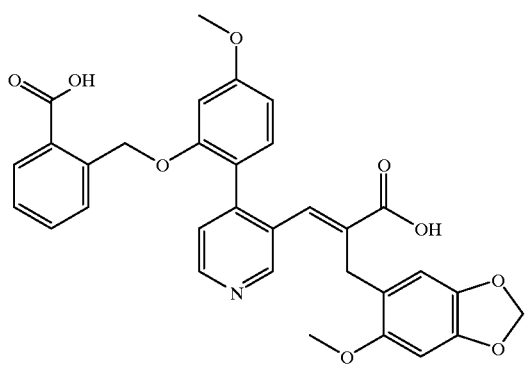

E-3-[4-[2-(2-Carboxypenyl)methoxy-4-methoxy]phenylpyridin-3-yl]-2-[2-methoxy-4, 5-methylenedioxybenzyl]prop-2-enoic acid a) 4-Chloro-3-formyl-pyridine In a flame-dried 3-necked 100 ml r.b. flask fitted with internal thermometer was prepared LDA at −78° using diisopropyl amine (2.8 ml, 19.9 mmol) and 2.5 M n-BuLi (8.32 ml, 20.8 mmol) in dry THF (15 ml). After stirring for 5 min, 4-chloropyridine (2.26 g, 19.9 mmol) in THF (5 ml) was added via a syringe pump at 0.15 ml/min over about 30 min. The mixture was stirred for 1 h, then dry DMF (4.8 ml, 62 mmol) was added via a syringe pump so that the temperature remained at −78°. After complete addition, the mixture was stirred 30 min then allowed to warm to −40° and hydrolyzed with 5% NaHCO$_3$. The mixture was extracted twice with t-butyl methyl ether and washed with 5% NaHCO$_3$, brine, dnred (MgSO$_4$), and concentrated. Chromatography (flash silica gel, 1:1 t-butyl methyl ether/hexanes) afforded the title compound as a white solid. (1.55 g, 55%).

EXAMPLE 5

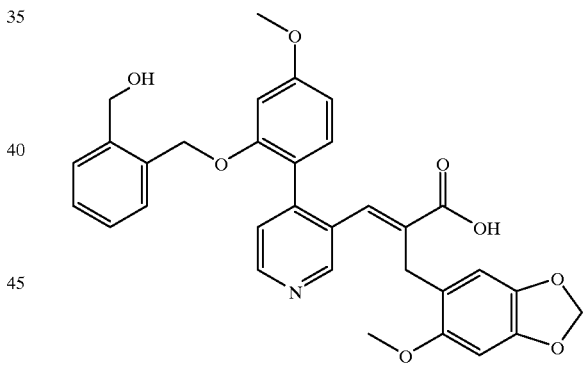

E-3-[4-[2-(2-Hyroxymethylphenyl)methoxy-4-methoxy]phenylpyridin-3-yl]-2-[2-methoxy-4, 5-methylenedioxybenzyl]prop-2-enoic acid Following the procedure of Example 4(a)–4(c) except substituting 2-hydroxy-methylbenzyl bromide for methyl-2-bromomethylbenzoate the title compound was prepared. (114 mg, 37%) (400 MHz, CDCl$_3$) δ 8.52 (d, 1H), 8.41 (s, 1H), 7.59 (s, 1H), 7.35 (d, J=6 Hz, 1H), 7.33–7.20 (m, 4H), 7.04 (d, J=8.4 Hz, 1H), 6.67 (d, J=2.1 Hz, 1H), 6.59 (dd, J=8.5 Hz, J=2.1 Hz, 1H), 6.43 (s, 2H), 5.84 (s, 2H), 5.09 (s, 2H), 4.55 (s, 2H) 3.85 (s, 3H), 3.62 (s, 3H), 3.35 (s, 2H); MS(ESP) m/e 556 [M+H]$^+$; MS(ESN) m/e 554 [M–H]$^-$; mp: 195–100° C.,; Anal. (C$_{32}$H$_{29}$NO$_8$.0.75 H$_2$O) calcd. C, 67.54; H, 5.40; N, 2.46: found. C, 67.65; H, 5.34; N, 2.64; HPLC t$_R$ 18.5 min, (Bakerbond Chiracel OC®; 25 cm×4.6 mm; hexane:ethanol, 85% with 0.1% TFA;

EXAMPLE 6

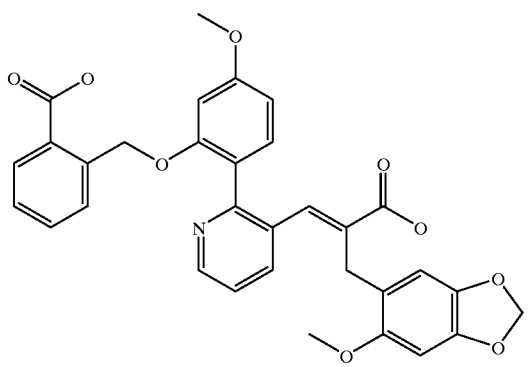

E-3-[2-[(2-Carboxypenyl)methoxy-4-methoxyphenyl]-pyridin-3-yl]-2-[2-methoxy-4, 5-methylenedioxybenzyl]prop-2-enoic acid a) Following the procedures in Example 4(b)–(c) except substituting 2-chloro-3-formyl-pyridine for 4-chloro-3-formyl-pyridine and for the preparation of E-Ethyl 3-[2 -[(2-Carbomethoxyphenyl)methoxy-4-methoxyphenyl]-pyridin-3-yl]-2-[2-methoxy-4,5-methylenedioxybenzyl] prop-2-enoate shown in Example 6 (b), the title compound was prepared as a tan solid. (58 mg, 10% )
(400 MHz, CDCl$_3$) δ 8.67 (d, J=3.5 Hz, 1H), 8.14 (d, J=7.8 Hz, 1H) 7.72 (s, 1H), 7.49–7.37 (m, 4H), 7.14 (dd, J=8.4 Hz, 4.8 Hz 1H), 6.71 (d, J=7.8 Hz, 1H), 6.70 (s, 1H), 6.48 (s, 1H), 6.43 (s, 1H), 5.85 (s, 2H), 5.49 (s, 2H), 3.89 (s, 3H), 3.71 (s, 3), 2.87 ( s, 2H); MS(ESP) m/e 570 [M+H]$^+$; MS(ESN) m/e 568 [M–H]$^-$; mp 135–140°; Anal. (C$_{32}$H$_{27}$NO$_9$.0.5 H$_2$O) calcd. C, 66.43; H, 4.88; N, 2.42: found. C, 66.47; H, 4.89; N, 2.40; HPLC t$_R$ 11.8 min. (Bakerbond Chiracel OC®; 25 cm×4.6 mm; hexane:ethanol, 80% with 0.1% TFA;
b) E-Ethyl 3-[2-[(2-Carbomethoxyphenyl)methoxy-4-methoxyphenyvl]-pyridin-3-yl]-2-[2-methoxy-4,5-methylenedioxybenzyl]prop-2-enoate.
A mixture of Ethyl 3-[2-(2-hydroxy-4-methoxy) phenylpyridin-3-yl]-2-(2-methoxy-4,5-methylenedioxybenzyl]-2-propenoate (340 mg, 0.69 mmol), silver oxide (170 mg, 0.73 mmol), and Carbomethoxybenzybromide (185 mg, 0.81 mmol) in acetonitrile were stirred under argon for 6 h at 60°. The mixture was cooled, filtered, and the solvent removed in vacuo. Chromatography (silica gel, 30–50% t-butyl methyl ether/hexanes afforded the title compound as a pale yellow solid.(104 mg, 25%).

EXAMPLE 7

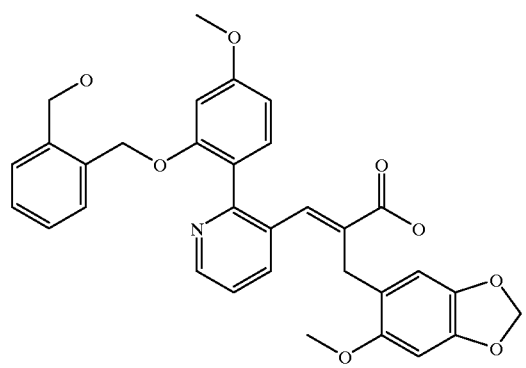

E-3-[2-[(2-Hydroxymethylphenyl)methoxy-4-methoxyphenyl]-pyridin-3-yl]-2-[2-methoxy-4, 5-methylenedioxybenzyl]prop-2-enoic acid Following the procedure of Example 6(a)–6(c) except substituting 2-hydroxy-methylbenzyl bromide for methyl-2-bromomethylbenzoate the title compound was prepared. (128 mg, 37%) (400 MHz, CDCl$_3$) δ 8.58 (d, J=4 Hz, 1H), 7.65 (s, 1H), 7.58 (d, J=8.4 Hz, 1H), 7.41 (d, J=7.5 Hz, 1H), 7.33–7.15 (m, 3H), 7.12 (d, J=8.4 Hz, 1H), 6.67 (s, 1H), 6.59 (d, J=8.5 Hz, 1H), 6.48 (s, 2H), 5.87 (s, 2H), 5.09 (s, 2H), 4.58 (s, 2H) 3.84 (s, 3H), 3.63 (s, 3H), 3.43 (s, 2H); MS(ESP) m/e 556 [M+H]$^+$; MS(ESN) m/e 554 [M–H]$^-$; mp 109.0–111.0; Anal. (C$_{32}$H$_{29}$NO$_8$.0.75 H$_2$O) calcd. C, 67.54; H, 5.40; N, 2.46: found. C, 67.42; H, 5.19; N, 2.35;

EXAMPLE 8

Formulations for pharmaceutical use incorporating compounds of the present invention can be prepared in various forms and with numerous excipients. Examples of such formulations are given below.

Inhalant Formulation

A compound of Formula I, (1 mg to 100 mg) is aerosolized from a metered dose inhaler to deliver the desired amount of drug per use.

| Tablets/Ingredients | Per Tablet |
| --- | --- |
| 1. Active ingredient (Cpd of Form. I) | 40 mg |
| 2. Corn Starch | 20 mg |
| 3. Alginic acid | 20 mg |
| 4. Sodium Alginate | 20 mg |
| 5. Mg stearate | 1.3 mg |
|  | 2.3 mg |

Procedure for tablets:

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

3 Step The wet mass is converted to granules by passing it through an oscillating granulator using a No. 8 mesh (2.38 mm) screen.

Step 4 The wet granules are then dried in an oven at 140° F (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of formula I in polyethylene glycol with heating. This solution is then diluted with water for injections Ph Eur. (to 100 ml). The solution is then steriled by filtration through a 0.22 micron membrane filter and sealed in sterile containers.

We claim:

1. A compound of Formula (I):

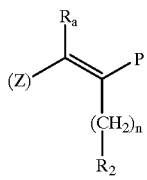

wherein Z is

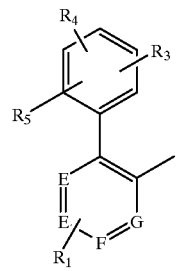

wherein D, E, F and G are N or $CR_1$ provided no more than one is nitrogen;

P is tetrazol-5-yl, $CO_2R_6$ or $C(O)N(R_6)S(O)_qR_{10}$;

$R_a$ is hydrogen or $C_{1-6}$alkyl;

$R_1$ is independently hydrogen, Ar, $C_{1-6}$alkyl, or $C_{1-6}$alkoxy;

$R_2$ is Ar, $C_{1-8}$alkyl, $(C(O)R_{14}$ or

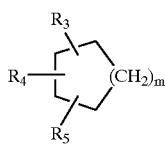

$R_3$ and $R_5$ are independently $R_{13}OH$, $C_{1-8}$alkoxy, $S(O)_qR_{11}$, $N(R_6)_2$, $NO_2$, Br, F, I, Cl, $CF_3$, $NHCOR_6$ $R_{13}CO_2R_7$, —X—$R_9$—Y, —$X(C(R_6)_2)OR_6$, —$(CH_2)_mX'R_8$ or —$X(CH_2)_nR_8$ wherein each methylene group within —$X(CH_2)_nR_8$ may be unsubstituted or substituted by one or two —$(CH_2)_nAr$ groups;

$R_4$ is independently $R_{11}$, OH, $C_{1-5}$alkoxy, $S(O)_qR_{11}$, $N(R_6)_2$, Br, F, I, Cl or $NHCOR_6$, wherein the $C_{1-5}$alkoxy may be unsubstituted or substituted by OH, methoxy or halogen;

$R_6$ is independently hydrogen or $C_{1-8}$alkyl;

$R_7$ is independently hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen or $XC_{1-10}$alkyl; or $R_7$ is $(CH_2)_nAr$;

$R_8$ is independently $R_{11}$, $CO_2R_7$, $CO_2C(R_{11})_2O(CO)XR_7$, $PO_3(R_7)_2$, $SO_2NR_7R_{11}$, $NR_7SO_2R_{11}$, $CONR_7SO_2R_{11}$, $SO_3R_7$, $SO_2R_7$, $P(O)(OR_7)R_7$, CN, $CO_2(CH_2)_mC(O)N(R_6)_2$, $C(R_{11})_2N(R_7)_2$, $C(O)N(R_6)_2$, $NR_7C(O)NR_7SO_2R_{11}$, $OR_6$, or tetrazole which is substituted or unsubstituted by $C_{1-6}$alkyl;

$R_9$ is independently a bond, $C_{1-10}$alkylene, $C_{1-10}$alkenylene, $C_{1-10}$alkylidene, $C_{1-10}$alkynylene, all of which may be linear or branched, or phenylene, all of which may be unsubstituted or substituted by one of more OH, $N(R_6)_2$, COOH or halogen;

$R_{10}$ is independently $C_{1-10}$alkyl, $N(R_6)_2$ or Ar;

$R_{11}$ is independently hydrogen, Ar, $C_{1-8}$alkyl, $C_{2-8}$alkenyl, $C_{2-8}$alkynyl, all of which may be unsubstituted or substituted by one or more OH, $CH_2OH$, $N(R_6)_2$ or halogen;

$R_{12}$ is independently hydrogen, $C_{1-6}$alkyl, $C_{2-6}$alkenyl or $C_{2-7}$alkynyl;

$R_{13}$ is independently divalent Ar, $C_{1-10}$alkylene, $C_{1-10}$alkylidene, $C_{2-10}$alkenylene, all of which may be unsubstituted or substituted by one or more OH, $CH_2OH$, $N(R_6)_2$ or halogen;

$R_{14}$ is independently hydrogen, $C_{1-10}$alkyl, $XC_{1-10}$alkyl, Ar or XAr;

$R_{15}$ is independently $C_{1-6}$alkyl or phenyl substituted by one or two $C_{1-6}$alkyl, OH, $C_{1-5}$alkoxy, $S(O)_qR_6$, $N(R_6)_2$, Br, F, I, Cl, $CF_3$ or $NHCOR_6$;

X is independently $(CH_2)_n$, O, $NR_6$ or $S(O)_q$;

X' is independently O, $NR_6$ or $S(O)_q$; Y is independently $CH_3$ or $X(CH_2)_nAr$;

Ar is independently:

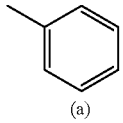

(a)

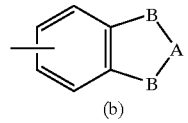

(b)

naphthyl, indolyl, pyridyl, thienyl, oxazolidinyl, thiazolyl, isothiazolyl, pyrazolyl, triazolyl, tetrazolyl, imidazolyl, imidazolidinyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more $Z_1$ or $Z_2$ groups;

A is independently C=O, or $(C(R_6)_2)_m$;

B is independently —$CH_2$— or —O—;

$Z_1$ and $Z_2$ are independently hydrogen, $XR_6$, $C_{1-8}$alkyl, $(CH_2)_qCO_2R_6$, $C(O)N(R_6)_2$, CN, $(CH_2)_nOH$, $NO_2$, F, Cl, Br, I, $N(R_6)_2$, $NHC(O)R_6$, $O(CH_2)_mC(O)NR_aSO_2R_{15}$, $(CH_2)_m$ $OC(O)NR_aSO_2R_{15}$, $O(CH_2)_mNR_aC(O))NR_aSO_2R_{15}$ or tetrazolyl which may be substituted or $O(CH_2)_mNR_aC(O)NR_aSO_2R_{15}$ or tetrazolyl which may be substituted by $C_{1-6}$alkyl, $CF_3$ or $C(O)R_6$;

m is independently 1 to 3;

n is independently 0 to 6;

q is independently 0, 1 or 2;

provided $R_3$ and $R_5$ are not O—O—$(CH_2)_nAr$ or O—O $R_6$;

or a pharmaceutically acceptable salt thereof.

2. A compound of Formula (I) wherein P is $CO_2R_6$; $R_1$ is hydrogen, $C_{1-6}$alkyl, or $C_{1-6}$ alkoxy; $R_2$ is Ar, cyclohexyl or $C_{1-4}$alkyl; $R_3$ and $R_5$ are independently hydrogen, $CO_2R_6$, OH, $C_{1-8}$alkoxy, $C_{1-8}$alkyl, $N(R_6)_2$, $NO_2$, Br, F, Cl, I, $R_{13}CO_2R_7$, $X(CH_2)_nR_8$, $(CH_2)_mX'R_8$, or $X(C(R_6)_2)_mOR_6$; $R_4$ is hydrogen, OH, $C_{1-5}$alkoxy, $N(R_6)_2$, Br, F, Cl, I, $NHCOCH_3$, or $S(O)_q$ $C_{1-5}$alkyl wherein the $C_{1-5}$alkyl may be unsubstituted or substituted by OH, methoxy or halogen; $R_6$ is hydrogen, methyl or ethyl; $R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_nAr$ wherein n is zero or 1 and Ar is substituted phenyl; $R_{11}$ is hydrogen, phenyl, pyridyl all of which may be substituted or unsubstituted by one or two $C_{1-4}$alkyl groups; $C_{1-8}$alkyl, $C_{2-8}$alkenyl, $C_{2-8}$-alkynyl, all of which may be substituted or unsubstituted by one or more OH, $CH_2OH$, $N(R_6)_2$, or halogen; $R_{12}$ is hydrogen or $C_{1-6}$alkyl; $R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen; $R_{15}$ is hydrogen or $C_{1-6}$alkyl; and D, E, F and G are N, or $CR_1$ provided no more than two are nitrogens.

3. A compound of claim 2 wherein P is $CO_2H$; $R_1$ is hydrogen, $C_{1-6}$alkyl, or $C_{1-6}$ alkoxy; $R_2$ is a group Ar wherein Ar is a group (a) or (b) and in said group (a) or (b), $Z_1$ and $Z_2$ are independently hydrogen, $CO_2R_6$, $(CH_2)_nOH$, $C_{1-4}$alkyl or $C_{1-6}$ alkoxy and A is $CH_2$, and one or both Bs are O; $R_3$ is Br, Cl, $C_{1-8}$alkoxy or $X(CH_2)_nR_8$, wherein X is O, n is 0, 1, or 2, and $R_8$ is selected from: $CO_2H$, OH, tetrazolyl optionally substituted by $C_{1-8}$alkyl; $CONR_7SO_2R_{11}$ wherein $R_7$ is H or $C_{1-8}$alkyl, $R_{11}$ is $C_{1-8}$alkyl or phenyl optionally substituted by Br, Cl, F, $C_{1-8}$alkyl; or $R_8$ is phenyl or pyridyl substituted by one or more Br, Cl, $CO_2H$, $CH_2OH$; $R_5$ is methoxy or $N(R_6)_2$ wherein $R_6$ is H or methyl; $R_4$ is hydrogen; $R_6$ is hydrogen, methyl or ethyl; $R_7$ is hydrogen, $C_{1-10}$alkyl, $C_{2-10}$alkenyl or $C_{2-8}$alkynyl, all of which may be unsubstituted or substituted by one or more OH, $N(R_6)_2$, $CO_2R_{12}$, halogen, or $R_7$ is $(CH_2)_nAr$ wherein $R_7$ is $(CH_2)_nAr$ and n is zero or 1 and Ar is phenyl substituted or unsubstituted by halogen or $C_{1-5}$ alkoxy; $R_{11}$ is hydrogen, phenyl, pyridyl wherein the phenyl or pyridyl be substituted or unsubstituted by one or two $C_{1-4}$alkyl groups; $C_{1-8}$alkyl, $C_{2-8}$alkenyl, $C_{2-8}$alkynyl, all of which may be substituted or unsubstituted by one or more OH, $CH_2OH$, $N(R_6)_2$, or halogen; $R_{12}$ is hydrogen or $C_{1-6}$alkyl; $R_{13}$ is phenyl, pyridyl, or $C_{2-10}$alkylene, all of which may be unsubstituted or substituted by one or more $CO_2R_6$, OH, $CH_2OH$, $N(R_6)_2$, or halogen; $R_{15}$ is hydrogen, ethyl, isopropyl, n-butyl, cyclopropylmethyl or cyclopropylethyl; and D, E, F and G are N, or $CR_1$ provided no more than two are nitrogens.

4. A compound of claim 1 selected from:
E-3-[4-[2-(2-Hydroxymethylphenyl)methoxy-4-methoxy]phenyl-5-propoxy-pyridin-3-yl]-2-[2-methoxy-4,5-methylenedioxybenzyl]prop-2-enoic acid;
E-3-[4-[2-(2-Carboxyphenyl)methoxy-4-methoxy]phenyl-5-propoxy-pyridin-3-yl]-2-[2-methoxy-4,5-methylenedioxybenzyl]prop-2-enoic acid; and
E-3-[2-[(2-Hydroxymethylphenyl)methoxy-4-methoxyphenyl]-pyridin-3-yl]-2-[2-methoxy-4,5-methylenedioxybenzyl]prop-2-enoic acid.

5. A pharmaceutical composition comprising a compound of claim 1 and a pharmaceutically acceptable carrier.

6. A method of treatment of diseases caused by an excess of endothelin comprising administering to a subject in need thereof, an effective amount of an endothelin receptor antagonist of claim 1.

7. A method of treating renal failure or cerebrovascular disease which comprises administering to a subject in need thereof, an effective amount of a compound of claim 1.

8. A method for the prophylaxis and treatment of radio-contrast induced renal failure which comprises administering to a subject in need thereof, an effective amount of a compound of claim 1.

9. A method of treatment of congestive heart failure which comprises administering to a subject in need thereof, an effective amount of a compound of claim 1.

10. A method of treatment of unstable angina, coronary vasospasm and myocardial savage which comprises administering to a subject in need thereof, an effective amount of a compound of claim 1.

11. A method of treating restenosis which comprises administering to a subject in need thereof, an effective amount of a compound of claim 1.

12. A method of treatment of pulmonary hypertension which comprises administering to a subject in need thereof, an effective amount of a compound of claim 1.

13. A method of treatment of stroke or subarachnoid hemorrhage which comprises administering to a subject in need thereof, an effective amount of a compound of claim 1.

14. A process for preparing a compound of claim 1 by:
(a) reaction of a compound of formula (II):

Formula (II)

wherein $R_{3a}$, $R_{4a}$ and $R_{5a}$ represent the groups $R_3$, $R_4$ and $R_5$ as defined for Formula (I) hereinabove, or a protected form or precursor thereof and $R_{1a}$ represents a group $R_1$ as defined for Formula (I) hereinabove, or a protected form or precursor thereof);
with a compound of Formula (III):

Formula (III)

wherein $R_2$ and P are as defined for formula (I) hereinabove and n is 0 to 5; followed if necessary or desired by:
(b) functional group interconversion of a compound of formula (I) into a different compound of formula (I) e.g.
(i) when formula (I) contains an ester group e.g. $CO_2R_6$, conversion to a corresponding compound wherein $R_6$ represents hydrogen;
(ii) when formula (I) contains a hydroxy group (e.g. in $R_3$, $R_4$ or $R_5$) conversion to a different group, eg a group $O(CH_2)Ar$ where Ar is as previously defined, by methods well known in the art; and/or
(c) salt formation.

* * * * *